US 6,632,330 B1

(12) United States Patent
Colley et al.

(10) Patent No.: US 6,632,330 B1
(45) Date of Patent: Oct. 14, 2003

(54) PROCESS FOR PURIFICATION OF ALKYL ALKANOATE

(75) Inventors: Stephen William Colley, Cleveland (GB); Norman Harris, County Durham (GB); Colin Rathmell, Cleveland (GB)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 09/806,112

(22) PCT Filed: Sep. 29, 1999

(86) PCT No.: PCT/GB99/03228

§ 371 (c)(1),
(2), (4) Date: Jun. 5, 2001

(87) PCT Pub. No.: WO00/20374

PCT Pub. Date: Apr. 13, 2000

(30) Foreign Application Priority Data

Oct. 1, 1998 (EP) .............................. 98308013

(51) Int. Cl.$^7$ .......................... B01D 3/40; C07C 67/54; C07C 69/14

(52) U.S. Cl. ............... 203/29; 203/18; 203/75; 203/55; 203/56; 203/57; 203/77; 203/78; 203/64; 203/80; 203/38; 560/248

(58) Field of Search ................ 203/74, 38, 77, 203/80, 18, 99, 75, DIG. 19, 64, 29, 58, 51, 78, 55, 56, 57; 568/913; 560/248

(56) References Cited

U.S. PATENT DOCUMENTS

| 2,524,899 | A |   | 10/1950 | Dunn |
| 4,379,028 | A |   | 4/1983  | Berg et al. |
| 4,395,576 | A | * | 7/1983  | Kwantes et al. ............. 568/913 |
| 4,481,146 | A | * | 11/1984 | Leupold et al. ................ 203/38 |
| 4,569,726 | A |   | 2/1986  | Berg et al. |
| 4,613,701 | A | * | 9/1986  | Strong ........................ 568/454 |
| 4,946,029 | A |   | 8/1990  | Frank et al. |

FOREIGN PATENT DOCUMENTS

| EP | 0 101 910 A1 | 3/1984 |
| EP | 0 151 886 A1 | 8/1985 |
| EP | 0 331 021 A1 | 9/1989 |

OTHER PUBLICATIONS

International Search Report for International Application No. PCT/GB 99/03228, mailed Jan. 21, 2000.

(List continued on next page.)

Primary Examiner—Virginia Manoharan
(74) Attorney, Agent, or Firm—Senniger, Powers, Leavitt & Roedel

(57) ABSTRACT

A process for the recovery of substantially pure alkyl alkanoate, such as ethyl acetate, from an impure feedstock. The impure feedstock is contacted with a selective hydrogenation catalyst in the presence of hydrogen in a selective hydrogenation zone maintained under selective hydrogenation conditions effective for selective hydrogenation of impurities containing reactive carbonyl groups thereby to hydrogenate the impurities to the corresponding alcohols. After recovery from the selective hydrogenation zone of a selectively hydrogenated reaction product mixture including the alkyl alkanoate and the corresponding alcohols, this is distilled in one or more distillation zones so as to produce substantially pure alkyl alkanoate therefrom which is recovered.

30 Claims, 3 Drawing Sheets

OTHER PUBLICATIONS

Engelhard Industries Division, *Hydrogenation of Carbonyl Compounds Over Platinum Metal Catalysts,* undated, 2 pages.

Edith Breitner, Eleanor Roginski and Paul N. Rylander, *Low Pressure Hydrogenation of Ketones with Platinum Metal Catalysts,* reprinted from the Journal of Organic Chemistry, 24, 1855 (1959), pp. 1–3.

Paul N. Rylander, *Catalytic Hydrogenation over Platinum Metals,* 1967, pp. 245, Academic Press, New York and London.

Engelhard Industries Division, *Engelhard Catalysts,* 1977, 3 pages.

Johnson Matthey Chemicals Limited, *Heterogeneous Catalysis Products and Services,* 1981–1984, 6 pages.

Alvin B. Stiles, *Catalyst Supports and Supported Catalysts,* 1987, pp. 132, Butterworth Publishers, Stoneham, MA.

Sami Matar, Manfred J. Mirbach, Hassan A. Tayla, *Catalysis in Petrochemical Processes,* 1989, pp. 260, Kluwer Academic Publishers, Dordrecht, Holland.

\* cited by examiner

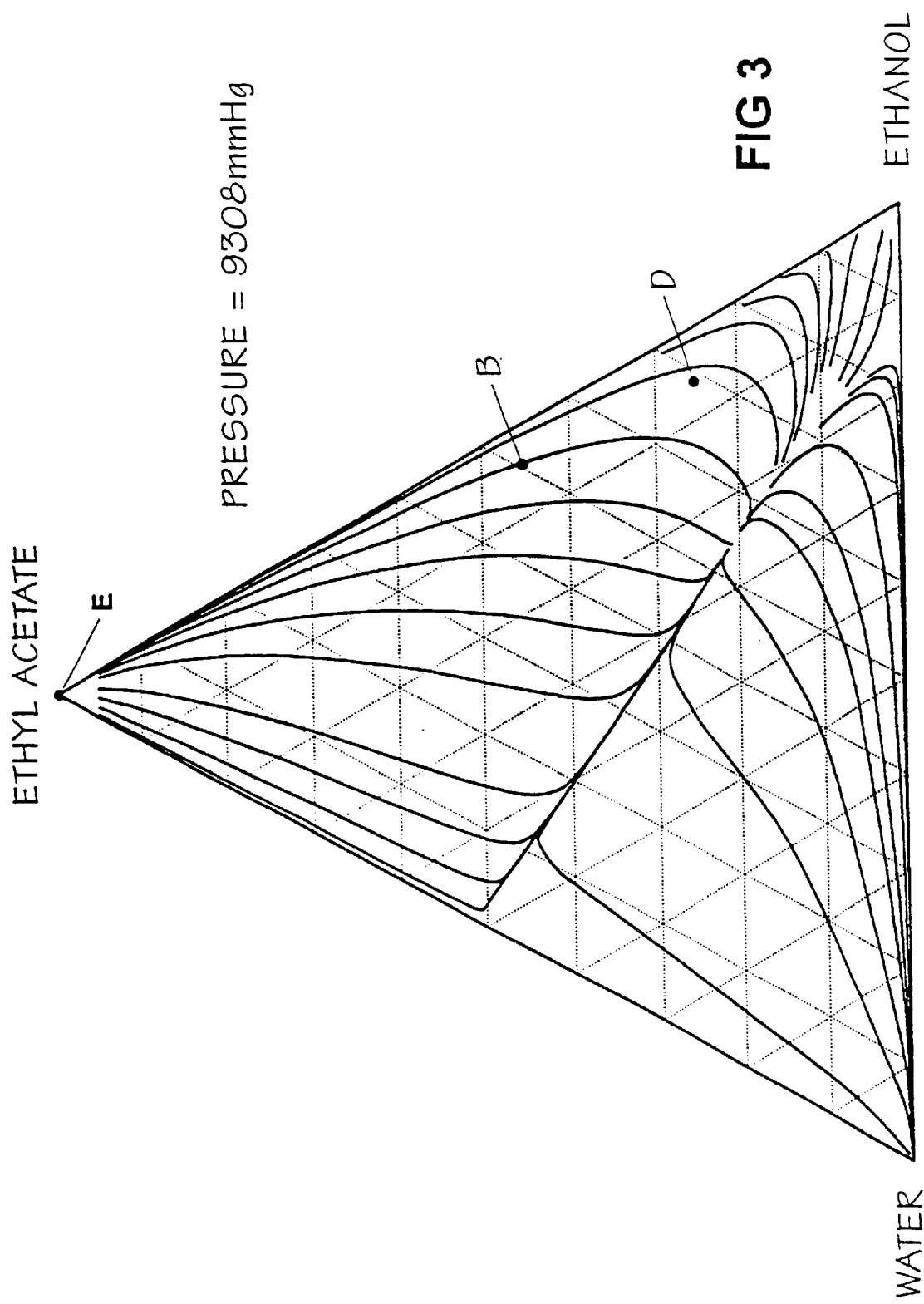

PROCESS FOR PURIFICATION OF ALKYL ALKANOATE

This invention relates to a process for purification of an impure feedstock containing an alkyl alkanoate which contains up to 12 carbon atoms as well as at least one impurity selected from an aldehyde and a ketone and containing the same number of carbon atoms as the alkyl alkanoate.

Alkyl alkanoates can be produced by esterification of an alkaroic acid with an alkanol. An example is the esterification of acetic acid with ethanol according to equation (1):

$$CH_3.CO.OH+CH_3CH_2OH=CH_3.CO.O.CH_2.CH_3+H_2O \quad (1)$$

Because the esterification reaction does not tend to lead to formation of by-products which have boiling points close to that of the alkyl alkanoate, recovery of substantially pure alkyl alkanoate from the esterification product mixture is usually not complicated by the presence of by-products of the esterification reaction.

Alkyl alkanoates can alternatively be produced using the Tischenko reaction. For example ethyl acetate can be produced from acetaldehyde according to the Tischenko reaction given in equation (2):

$$2CH_3.CHO=CH_3.CO.O.CH_2.CH_3 \quad (2).$$

It is also possible to produce alkyl alkanoates from alkanols by dehydrogenation. For example ethyl acetate can be made from ethanol by dehydrogenation according to equation (3):

$$2CH_3.CH_2.OH=CH_3.CO.O.CH_2.CH_3+2H_2 \quad (3).$$

Catalytic dehydrogenation of alcohols with reduced copper under ultra violet light was described by S. Nakamura et al, in *Bulletin of the Chemical Society of Japan* (1971), Vol. 44, pages 1072 to 1078.

K. Takeshita et al described reduced copper catalysed conversion of primary alcohols into esters and ketones in *Bulletin of the Chemrical Society of Japan*, (1978) Vol. 51(9), pages 2622 to 2627. These authors mention that the mechanism for ester formation has been described in the literature as the Tischenko reaction. That is to say that dehydrogenation of ethanol yields acetaldehyde as an intermediate which combines according to the Tischenko reaction to produce ethyl acetate. Alternatively, or as well, 1 mole of ethanol may combine with 1 mole of acetaldehyde to yield 1 mole of ethyl acetate and 1 mole of hydrogen according to equation (4):

$$CH_3CH_2OH+CH_3.CHO=CH_3.CO.O.CH_2.CH_3+H_2 \quad (4).$$

Production of esters from primary alcohols by dehydrogenation using bromous acid or a salt thereof in acid medium is described in JP-A-59/025334.

In SU-A-362814 there is described a process for production of ethyl acetate by dehydrogenation of ethanol at 180° C. to 300° C. in the presence of a copper catalyst containing zinc as an activator with an ethanol feed rate of 250 to 700 liters per liter of catalyst per hour.

The dehydrogenation of ethanol to form ethyl acetate is described in GB-A-287846. This proposes use of a dehydrogenating agent, such as a copper catalyst, a temperature of from 250° C. to 500° C., and a pressure of more than 10 atmospheres ($1.013\times10^6$ Pa)

Vapour phase contact of ethanol at a temperature above its critical temperature with a catalyst comprising copper and a difficultly reducible oxide, such as zinc oxide or manganese oxide, is proposed in GB-A-312345 for the production of ethyl acetate, use of a temperature of 375° C. and a pressure of 4000 psi (27.58 Mpa) being suggested.

GB-A-470773 teaches a process for conversion of ethanol to ethyl acetate by dehydrogenating ethanol over a catalyst consisting of a reduced metal, for example, copper on infusorial earth with 10% uranium oxide as promoter, maintained at a temperature of 220° C. to 260° C. , removing by condensation some of the gas-vapour product rich in hydrogen resulting from the reaction, and returning the gaseous remainder rich in hydrogen to the catalysing zone.

EP-A-0151886 describes a process for the preparation of $C_{2+}$ esters of alkyl carboxylic acids from $C_{2+}$ primary alcohols which comprises contacting a vaporous mixture containing a primary $C_{2+}$ alkanol and hydrogen in an alkanol:hydrogen molar ratio of from 1:10 to about 1000:1 at a combined partial pressure of alkanol and hydrogen of from about 0.1 bar ($10^3$ Pa) up to about 40 bar ($4\times10^6$ Pa) and at a temperature in the range of from about 180° C. to about 300° C. in a catalytic reaction zone with a catalyst consisting essentially of a reduced mixture or copper oxide and zinc oxide, and recovering a reaction product mixture containing a primary $C_{2+}$ alkyl ester of an alkyl carboxylic acid which ester contains twice as many carbon atoms as the primary $C_{2+}$ alkanol.

In EP-A-0201105 there is described a method for converting primary alcohols, such as ethanol, to their corresponding alkanoate esters which involves the regulation of the mole feed ratio of hydrogen gas to alkanol in the reaction zone of a copper chromite containing catalyst.

Separation of ethyl acetate from a composition comprising ethyl acetate, ethanol and water is disclosed in JP-A-05/186392 by feeding the composition to a distillation column to obtain a quasi-azeotropic mixture comprising ethyl acetate, ethanol and water, condensing it, separating the condensate into an organic layer and an aqueous layer, returning the organic layer to the column, and recovering ethyl acetate as a bottom product from the column.

EP-A-0331021 describes how carbonylation of olefins to produce monocarboxylate esters causes formation of aldehydes and acetals as byproducts. Monocarboxylate esters produced in this way are subjected to a three step purification process involving treatment with a strongly acidic agent, followed by hydrogenation and distillation. The initial treatment with a strongly acidic agent is intended to convert acetals to vinyl ethers and aldehydes and acetals to aldols. The subsequent hydrogenation step then converts these compounds to byproducts which are more easily separated from the desired monocarboxylate ester.

EP-A-0101910 contains a similar disclosure regarding carbonylation of olefins to give monocarboxylate esters. It proposes treatment of the monocarboxylate ester with hydrogen at elevated temperature in the presence of an acidic ion exchanger or zeolite doped with one or more metals of Group VIII of the Periodic Table, followed by hydrogenation. It is stated that acetals present as byproducts are converted to vinyl ethers which are converted by hydrogenation to low boiling esters or the aldehydes and acetals are converted to high boilers by an aldol reaction. Unsaturated ketones are converted to saturated ketones.

One particular problem in production of alkyl alkanoates by dehydrogenation of an alkanol is that the reaction product mixture tends to be a complex mixture including esters, alcohols, aldehydes and ketones. The reaction product mixtures contain components with boiling points close to that of the desired alkyl alkanoate or alkanoates. In some cases such components can form azeotropes, including azeotropes with the desired alkyl alkanoate or alkanoates whose boiling points are close to that of the alkyl alkanoate or alkanoates. This is a particular problem when a high purity alkyl alkanoate, such as ethyl acetate, is desired.

The present invention accordingly seeks to provide a novel process for recovery of a substantially pure alkyl alkanoate from an impure feedstock, for example a crude product produced by dehydrogenation of an alkanol which contains by-products whose boiling point is close to that of the desired alkyl alkanoate or alkanoates and which, in some cases at least, from azeotropes with the alkyl alkanoate or alkanoates whose boiling points are close to that of the desired alkyl alkanoate or alkanoates. It further seeks to provide a process for purification of an impure feedstock containing an alkyl alkanoate containing up to 12 carbon atoms which further contains as an impurity at least one aldehyde and/or ketone which contains the same number of carbon atoms as the alkyl alkanoate so as to result in production of a substantially pure alkyl alkanoate product. In addition the invention seeks to provide an improved process for the production of an alkyl alkanoate by dehydrogenation or oxidation of an alkanol, by reaction of an alkanol with an alkanal, or by oxidation of an alkanol to an alkanal followed by the Tischenko reaction which enables production of a substantially pure alkyl alkanoate product, despite the presence in the crude reaction product of aldehydes and ketones which would otherwise contaminate the alkyl alkanoate product.

According to the present invention there is provided a process for the purification of an impure feedstock comprising an alkyl alkanoate which contains up to 12 carbon atoms which comprises:

(a) providing an impure feedstock containing an alkyl alkanoate which contains up to 12 carbon atoms, said feedstock further containing at least one impurity which is selected from an aldehyde and a ketone and which contains the same number of carbon atoms as said alkyl alkanoate;

(b) contacting said impure feedstock with a selective hydrogenation catalyst in the presence of hydrogen in a selective hydrogenation zone maintained under selective hydrogenation conditions effective for selective hydrogenation of impurities containing reactive carbonyl groups thereby to hydrogenate said impurities to the corresponding alcohols;

(c) recovering from the selective hydrogenation zone a selectively hydrogenated reaction product mixture comprising said alkyl alkanoate, hydrogen, and said corresponding alcohols;

(d) distilling material of the selectively hydrogenated reaction product mixture in one or more distillation zones so as to produce substantially pure alkyl alkanoate therefrom; and (e) recovering said substantially pure alkyl alkanoate.

The invention further provides a process for the production of an alkyl akanoate containing up to 12 carbon atoms by dehydrogenation of an alkanol which comprises: (i) contacting a vaporous mixture containing an
alkanol and hydrogen with a dehydrogenation catalyst in a dehydrogenation zone maintained under dehydrogenation conditions effective for dehydrogenation of an alkanol to yield an alkyl alkanoate containing up to 12 carbon atoms;

(ii) recovering from the dehydrogenation zone an intermediate reaction mixture comprising hydrogen and liquefiable products comprising said alkyl alkanoate, said alkanol, hydrogen and by-products containing reactive carbonyl groups; and (iii) subjecting at least a portion of the liquefiable products of the intermediate reaction product mixture as impure feedstock to a process as outlined in the preceding paragraph.

The impure feedstock may be effectively any feedstock which contains an alkyl alkanoate, such as ethyl acetate, or a mixture of alkyl alkanoates, possibly water, an alkanol, such as ethanol, or a mixture of alkanols, and minor amounts of impurities including aldehydes and/or ketones. In the case of ethyl acetate such aldehydes and ketones include n-butyraldehyde, acetone and butan-2-one. Example of such an impure feedstock are the intermediate reaction product mixtures obtained by dehydrogenation of an alkanol, such as ethanol, or of a mixture of alkanols, such as ethanol and iso-butanol.

A range of undesirable impurities may be present in the feedstock, some of which would cause separation problems if the feedstock were to be directly refined because their boiling points are close to that of the alkyl alkanoate or because, in some cases at leas, they form azeotropes with the alkyl alkanoate whose boiling point is close to that of the alkyl alkanoate. For example, purification of the specified exemplary alkyl alkanoates can be complicated by the presence of the impurities set out in the following Table 1, the same impurities generally giving rise to problems with all alkyl alkanoates with the same number of carbon atoms.

TABLE 1

| No. of C atoms | Alkyl alkanoate | b.p. (° C.) | Impurity | b.p. (° C.) |
|---|---|---|---|---|
| 2 | Methyl formate | 31.5 | Acetaldehyde | 20 |
|   |   |   | Propionaldehyde | 48 |
| 3 | Ethyl formate | 54.5 | Propionaldehyde | 48 |
|   | Methyl acetate | 56.2 | Acetone | 56 |
| 4 | Ethyl acetate | 77 | n-butyraldehyde | 75 |
|   | Methyl propionate | 79 | Butan-2-one | 80 |
|   | n-propyl formate | 81.3 |   |   |
| 5 | Methyl butyrate | 103.6 | n-valeraldehyde | 103 |
|   | Ethyl propionate | 100 | Pentan-2-one | 102 |
|   | n-propyl acetate | 101.6 | Pentan-3-one | 102 |
|   | n-butyl formate | 107.5 |   |   |
| 6 | Methyl valerate | 127 | n-hexanal | 128 |
|   | Ethyl butyrate | 123 | Hexan-2-one | 128 |
|   | n-propyl propionate | 123 | Hexan-3-one | 124 |
|   | n-butyl acetate | 126 |   |   |
|   | n-pentyl formate | 132 |   |   |
| 7 | Methyl caproate | 150 | n-heptanal | 152 |
|   | Ethyl valerate | 146 | Heptan-2-one | 151 |
|   | n-propyl butyrate | 145 | Heptan-3-one | 147 |
|   | n-butyl propionate | 146 | Heptan-4-one | 144 |
|   | n-pentyl acetate | 149 |   |   |
|   | n-hexyl formate | 156 |   |   |

It will be appreciated by those skilled in the art that Table 1 lists only some of the possible alkyl alkanoates whose production is embraced within the teachings of the present invention. For example, isomeric alkyl alkanoates derived from alkanols and/or alkanoic acids with branched chains can also be mentioned.

Preferably the alkyl alkanoate is a $C_2$ to $C_4$ alkyl ester of a $C_2$ to $C_4$ alkanoic acid, for example, ethyl acetate, n-propyl propionate, or n-butyl butyrate.

For convenience the process will hereafter be described in relation to Durification of impure ethyl acetate feedstocks.

In the case of an impure feedstock resulting from dehydrogenation of ethanol, the ethanol feedstock may contain impurities or impurities may be formed as by-products in the production of the alkyl alkanoate, for example, in the course of the dehydrogenation step. Problematical impurities are aldehydes and ketones, such as n-butyraldehyde and butan-2-one in the case of ethyl acetate. In order to minimise problems due to the presence of such impurities in the distillation step (d) even in amounts as small as about 0.1 mol % or less, e.g. about 0.01 mol % or less, problematical impurities are substantially removed as a result of the selective hydrogenation step (b). Accordingly, the impure feedstock is contacted in admixture with hydrogen in step (b) with a selective hydrogenation catalyst. The catalyst type and reaction conditions are chosen so that aldehydes and ketones are hydrogenated to their respective alcohols, while hydrogenation of the alkyl alkanoate, e.g. ethyl acetate, is minimal. Among aldehyde and ketone impurities which may be present in an impure ethyl acetate feedstock, butan-2-one and n-butyraldehyde, in particular, would otherwise cause problems in any subsequent distillation. These compounds are hydrogenated in the selective hydrogenation zone in step (b) to the corresponding alcohols, i.e. 2-butanol and n-butanol respectively, which can be readily separated from ethyl acetate by distillation.

The mixture supplied to the selective hydrogenation zone in step (b) contains, in addition to ethanol, hydrogen either alone or in admixture with one or more inert gases that are inert to the reactants and catalysts in the selective hydrogenation step (b) of the process of the invention. Examples of such inert gases are nitrogen, methane, and argon. The source of the hydrogen used in the selective hydrogenation step (b) may be hydrogen formed in the dehydrogenation step and accordingly may include gas recycled from the downstream end of the selective hydrogenation zone as described further below.

The selective hydrogenation step (b) is typically conducted at a temperature of from about 40° C. to about 120° C., preferably at a temperature in the range of from about 60° C. to about 80° C.

Typical selective hydrogenation conditions include use of a feedstock:hydrogen molar ratio of from about 1000:1 to about 5:1, for example about 20:1.

The combined partial pressure of feedstock and hydrogen in the selective hydrogenation zone typically lies in the range of from about 5 bar ($5 \times 10^5$ Pa) up to about 80 bar ($8 \times 10^6$ Pa), and is even more typically about 24 bar ($2.5 \times 10^6$ Pa) to about 50 bar ($5 \times 10^6$ Pa)

The selective hydrogenation catalyst used in step (b) of the process of the invention is selected to have good activity for hydrogenation of reactive carbonyl containing compounds, but relatively poor ester hydrogenation activity. Suitable catalysts comprise metals selected from nickel, palladium and platinum. Ruthenium, supported on carbon, alumina or silica is also effective, as are other metal catalysts such as rhodium and rhenium. Preferred catalysts include nickel on alumina or silica and ruthenium on carbon. Particularly preferred catalysts include 5% ruthenium on carbon available from Engelhard.

The rate of supply of impure feedstock to the selective hydrogenation zone typically corresponds to a liquid hourly space velocity (LHSV) of from about 0.1 hr$^{-1}$ to about 2.0 hr$^{-1}$, preferably from about 0.2 hr$^{31\ 1}$ to about 1.5 hr$^{-1}$. When using a nickel containing catalyst the LHSV may be, for example, from about 0.3 hr$^{-1}$ to about 0.5 hr$^{-1}$.

Step (c) of the process of the present invention comprises recovering from the selective hydrogenation zone a selectively hydrogenated reaction product mixture comprising alkyl alkanoate (e.g. ethyl acetate), alkanol (e.g. ethanol), hydrogen and hydrogenated impurities. Typically this includes a condensation stem in order to separate liquefiable materials from a gaseous stream containing unreacted hydrogen which can be recycled for dehydrogenation or for selective hydrogenation.

The impure feedstock typically contains water and alkanol (e.g. ethanol) in addition to alkyl alkanoate (e.g. ethyl acetate). In this case step (d) of the process of the invention comprises distilling material of the selectively hydrogenated reaction product mixture in one or more distillation zones. When the alkyl alkanoate is ethyl acetate, distillation is effected so as to produce a first composition comprising substantially pure ethyl acetate and a second composition comprising ethanol and water. In this step the selectively hydrogenated reaction product mixture subjected to distillation typically has a water content of less than about 20 mol %, more usually not more than about 15 mol %.

Ethanol, water and ethyl acetate form a minimum boiling ternary azeotrope upon distillation thereof.

One method of separating ethyl acetate from ethanol and water involves extractive distillation with an extractive agent comprising polyethylene glycol and dipropylene glycol, diethylene glycol, or triethylene glycol as described in U.S. Pat. No. 4569726 or with an extractive agent containing dimethyl sulfoxide as described in U.S. Pat. No. 4379028. Hence step (d) may comprise an extractive distillation procedure.

Preferably, however, distillation is carried out in step (d) by a procedure which takes advantage of the fact that the composition of the minimum boiling ternary azeotrope formed by ethanol, water and ethyl acetate depends upon the pressure at which distillation is effected. Hence a preferred distillation procedure comprises supplying material of the selectively hydrogenated reaction product mixture to a first distillation zone maintained under distillation conditions effective for distillation therefrom of a first distillate comprising ethyl acetate, ethanol, and water, recovering a first distillate comprising ethyl acetate, ethanol, and water from the first distillation zone and a bottom product comprising ethanol and water, supplying material of the first distillate to a second distillation zone maintained under distillation conditions effective for distillation therefrom of a second distillate comprising ethanol, water, and ethyl acetate (preferably a minor amount of ethyl acetate) and so as to yield a substantially pure ethyl acetate bottom product, and recovering a substantially pure ethyl acetate bottom product from the second distillation zone. The first distillation zone is preferably operated at a pressure less than about 4 bar ($4 \times 10^5$ Pa), preferably from about 1 bar ($10^5$ Pa) up to about 2 bar ($2 \times 10^5$ Pa), while the second distillation zone is operated at a higher pressure than that of the first distillation zone, for example at a pressure of from about 4 bar ($4 \times 10^5$ Pa) to about 25 bar ($2.5 \times 10^6$ Pa), preferably from about 9 bar ($9 \times 10^5$ Pa) to about bar ($15 \times 10^5$ Pa).

It can be shown that in this Dreferred distillation procedure the rate of flow of the first distillate from the first distillation zone to the second distillation zone and the corresponding flow rate from the second distillation zone to the first distillation zone of the second distillate can be minimised by operating one of the distillation zones so that the distillate has a composition very close to that of the ternary azeotrope at that pressure. However, in order to operate that zone so that the distillate has a composition close to that of the ternary azeotrope at its pressure of operation, a high degree of separation is required which necessitates use of a distillation column with many distillation trays and a high heat input. In addition, since water has the highest latent heat of vaporisation out of the three components of the ternary azeotrope, the total heat input to the two zones can be minimised by minimising the water content of the feeds to the distillation zones.

In addition to forming a ternary azeotrope, the three components of the ternary azeotrope can each also form binary azeotropes with one of the other components. For example, ethanol forms a binary azeotrope with water and also with ethyl acetate it is preferred to select a pressure of operation of the second distillation zone so that the binary azeotrope between ethanol and ethyl acetate at that pressure has a lower ethyl acetate content than the ternary azeotrope at that pressure and further to select a pressure of operation for the first distillation zone and to adjust the flow rates of the distillates between the first and second zones so that the first distillate has as low a water content as possible. In this way the second distillate recovered from the second distillation zone low content of ethyl acetate.

In the preferred distillation procedure an ethanol rich stream containing substantially all of the water in the selectively hydrogenated reaction mixture is recovered from the bottom of the first distillation zone, while an overhead stream that contains "light" components present in the selectively hydrogenated reaction product mixture is recovered from the first distillation zone, and the first distillate comprises a liquid draw stream which is recovered from an upper region of the first distillation zone and which comprises ethyl acetate, ethanol, water and minor amounts of other components. By the term "light" components is meant components that have lower boiling points than ethyl acetate and its azeotropes with water and ethanol. The liquid draw stream typically contains less than about mol 10% water. For example, it suitably comprises from about 1 mol % to about 6 mol % water, from about 40 mol % to about 55 mol % ethyl acetate, not more than about 2 mol a minor products (preferably not more than about 1 mol % minor products) and the balance ethanol. Thus it may typically contain about 45 mol % ethyl acetate, about 50 mol % ethanol, about 4 mol % water and about 1 mol % other components. This liquid draw stream is passed to the second distillation zone. The second distillate, with a typical composition of about 25 mol % ethyl acetate, about 68 mol % ethanol, about 6 mol % water, and about 1 mol % of other components, is recovered as an overhead stream from the second distillation zone, while a bottom product comprising ethyl acetate is recovered from the second distillation zone which typically contains from about 99.8 mol % to about 99.95 mol % ethyl acetate; this second distillate is returned to the first distillation zone, preferably at a point above the feed point of the liquefiable products of the selectively hydrogenated reaction product mixture.

The overhead stream from the first distillation zone contains "light" components present in the intermediate reaction product mixture, such as diethyl ether, acetaldehyde and acetone. It can be burnt as a fuel.

In this preferred process of the invention the ethanol rich stream recovered from the bottom of the first distillation zone can, if desired, be subjected to treatment for the removal of water therefrom thereby to produce a relatively dry ethanol stream which can be used for a purpose which will be described below, if desired. products, including unknown products, with high boiling points compared to those of ethanol and ethyl acetate. These can be separated from the ethanol and water by distillation, if desired, prior to effecting removal of water from the resulting distillate. The resulting ethanol stream, after water removal, can be recycled for production of further ethyl acetate.

One suitable method for removal of water from the ethanol rich stream or from the distillate resulting from "heavies" removal is molecular sieve adsorption. Azeotropic distillation with a suitable entrainment agent, such as benzene or cyclohexane, can alternatively be used. Membranes are currently under development which will enable separation of water from ethanol; these are reported to be nearly ready for commercial exploitation. Hence use of a membrane is another option available for separating water from the ethanol rich stream.

Preferably the water content of the thus produced relatively dry ethanol is less than about 5 mol %, and preferably less than about 2 mol %.

The impure alkyl alkanoate feedstock may, for example, comprise liquefiable components of a reaction product mixture produced by dehydrogenation of ethanol. Such ethanol may have been produced by hydration of ethylene, by the Fischer Tropsch process, or by fermentation of a carbohydrate source, such as starch (for example, in the form of a corn steep liquor) It may alternatively be a by-product of another industrial process. It may contain, besides ethanol, minor amounts of water as well as small amounts of impurities resulting from by-product formation during its synthesis. If there is provision for recycle of recovered ethanol, then any by-products formed during production of ethyl acetate will contribute to the level of by-products present in the feedstock. Impurities present in the ethanol feedstock may include, for example, higher alcohols such as n-propanol, iso-propanol, n-butanol and sec-pentanol; ethers, such as diethyl ether, and di-iso-propyl ether; esters, such as iso-propyl acetate, sec-butyl acetate and ethyl butyrate; and ketones, such as acetone, butan-2-one, and 2-pentanone. At least some of these impurities can be difficult to remove from ethyl acetate, even when they are present in quantities as low a about 0.1 mol % or less, by traditional distillation procedures because they have boiling points which are close to that of ethyl acetate and/or form distillates therewith.

In the dehydrogenation step ethanol can be converted to ethyl acetate by a dehydrogenation procedure which comprises contacting a vaporous mixture containing ethanol and hydrogen with a dehydrogenation catalyst in a dehydrogenation zone maintained under dehydrogenation conditions effective for dehydrogenation of ethanol to yield ethyl acetate.

Typical dehydrogenation conditions include use of an ethanol:hydrogen molar ratio of from about 1:10 to about 10000:1, a combined partial pressure of ethanol and hydrogen of up to about 50 bar ($5 \times 10^6$ Pa), and a temperature in the range of from about 100° C. to about 260° C.

Preferably the combined partial pressure of ethanol and hydrogen ranges from about 3 bar ($3 \times 10^5$ Pa) up to about 50 bar ($5 \times 10^6$ Pa), and is more preferably at least 6 bar ($6 \times 10^5$ Pa) up to about 30 bar ($3 \times 10^6$ Pa), and even more preferably in the range of from about 10 bar ($10^6$ Pa) up to about 20 bar ($2 \times 10^6$ Pa), for example about 12 bar ($1.2 \times 10^6$ Pa).

Dehydrogenation is preferably conducted in the dehydrogenation zone at a temperature of from about 200° C. to about 250° C., preferably at a temperature in the range of from about 210° C. to about 240° C., even more preferably at a temperature of about 220° C.

The ethanol:hydrogen molar ratio in the vaporous mixture fed into contact with the dehydrogenation catalyst usually will not exceed about 400:1 or about 500:1 and may be no more than about 50:1.

The dehydrogenation catalyst is desirably a catalyst containing copper, optionally in combination with chromium, manganese, aluminum, zinc, nickel or a combination of two or more of these metals, such as a copper, manganese and aluminium containing catalyst. Preferred catalysts comprise, before reduction, copper oxide on alumina, an example of which is the catalyst sold by Mallinckrodt Specialty Chemicals, Inc., under the designation E408Tu, a catalyst which contains 8% by weight of alumina. Other preferred catalysts include chromium promoted copper catalysts available under the designations PG85/1 (Kvaerner Process Technology Limited) and CU0203T (Engelhard), manganese promoted copper catalysts sold under the designation T4489 (Süd Chemie AG), and supported copper catalysts sold under the designation D-32-J (Süd Chemie AG). E408Tu is a particularly preferred dehydrogenation catalyst.

In the dehydrogenation step the rate of supply of the ethanol feedstock to the dehydrogenation zone typically corresponds to an ethanol liquid hourly space velocity (LHSV) of from about 0.5 hr$^{-1}$ to about 1.0 hr$^{-1}$.

Hydrogen is produced as a result of the dehydrogenation reaction and can be recycled to the dehydrogenation zone from downstream in the process. The hydrogen can be substantially pure hydrogen or can be in the form of a mixture with other gases that are inert to the ethanol feedstock and to the dehydrogenation catalyst. Examples of such other gases include inert gases such as nitrogen, methane and argon.

In the dehydrogenation zone, side reactions may also occur, including formation of water. It is postulated that such side reactions, in the case of production of ethyl acetate, include formation of acetaldehyde which in turn can undergo aldol formation, followed by dehydration to form an unsaturated alcohol and water. These reactions can be summarised thus:

$$CH_3CH_2OH = CH_3CHO + H_2 \quad (5)$$

$$2CH_3CHO = CH_3CH(OH)CH_2CHO \quad (6)$$

and $$CH_3CH(OH)CH_2CHO = CH_3CH = CHCHO + H_2O \quad (7).$$

The crotonaldehyde produced by equation (7) can then undergo hydrogenation to form n-butanol thus:

$$CH_3CH = CHCHO + H_2 = CH_3CH_2CH_2CH_2HO. \quad (8)$$

Other side reactions which release water as a by-product include formation of ketones, such as acetone and butan-2-one, and formation of ethers, such as diethyl ether.

In such a dehydrogenation process there is recovered from the ethyl acetate production zone an intermediate reaction product mixture comprising hydrogen and liquefiable products comprising ethyl acetate, ethanol, hydrogen and by-products containing reactive carbonyl groups; this intermediate reaction product mixture can be used as impure feed to the recovery process of the invention. The step of recovering this intermediate reaction product mixture can be effected in any convenient manner and may include a condensation step in order to condense liquefiable products present in the intermediate reaction product mixture. Alternatively the intermediate reaction product can be passed directly to step (b) without any intermediate condensation step.

The production of a relatively dry ethanol stream has been mentioned above. This can be recycled, if desired, to the dehydrogenation step, if used, or can be used for any other desired purpose.

In order that the invention may be clearly understood and readily carried into effect, a preferred form of plant for the production of ethyl acetate, and a process in accordance with the invention will now be described, by way of example only, with reference to the accompanying drawings, wherein:

FIGS. 2 and 3 are triangular diagrams illustrating the boiling behaviour of ternary mixtures of ethanol, water and ethyl acetate at two different pressures.

Figure 1:
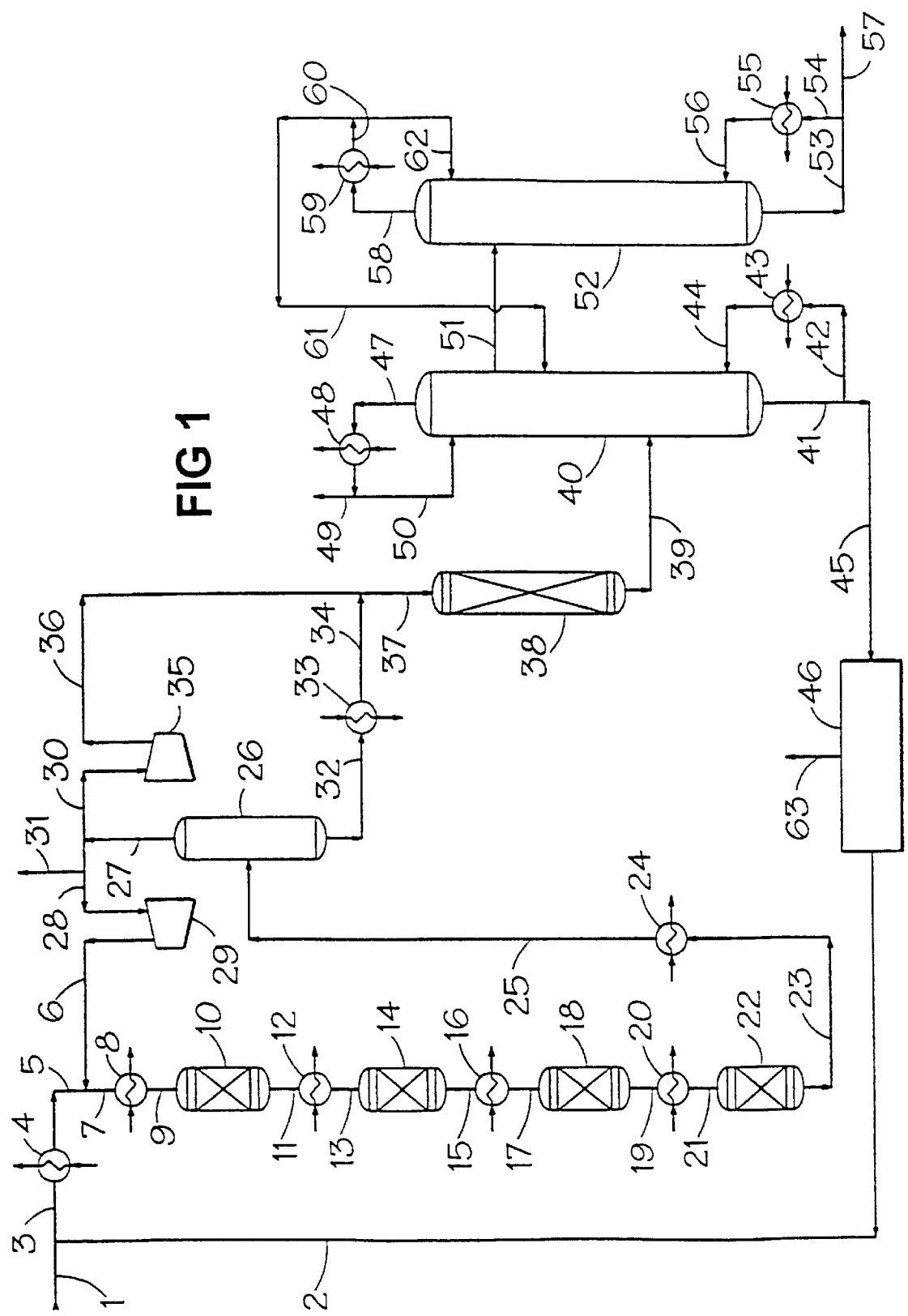
FIG. 1 is a flow diagram of a plant for the production of ethyl acetate constructed to operate a process in accordance with the invention.

Referring to FIG. 1 of the drawings, it will be appreciated by those skilled in the art that, since the drawing is diagrammatic, many conventional items of equipment, such as pumps, surge drums, flash drums, heat exchangers, temperature controllers, pressure controllers, holding tanks, temperature gauges, pressure gauges, and the like, which would be required in an operating plant, have been omitted for the sake of simplicity. Such items of equipment would be incorporated in an actual plant in accordance with standard chemical engineering practice and form no part of the present invention. Moreover there are many ways of effecting heat exchange and the depiction of separate heat exchangers each with its own heating or cooling line does not necessarily mean that single heat exchanger units are necessary. Indeed in many cases it may be more practicable and economic to use two separate heat exchangers instead of one with a step change in temperature occurring in each. It is also practicable to use conventional heat recovery techniques so as to recover heat from, or to increase the temperature of, one stream by heat exchange with another stream of the plant.

In the plant of FIG. 1 a stream of crude ethanol is pumped to the plant from a suitable holding tank (not shown) in line 1 at a pressure of 16.2 bar absolute (16.2×10$^5$ Pa) and at a temperature of approximately 30° C. and is admixed with recycled material from line 2. The resulting mixture in line 3 is heated by means of heat exchanger 4 to a temperature of 166° C. thereby forming a vaporous stream which passes on in line to be mixed with a stream of hydrogen from line 6. The resulting mixture passes on in line 7, is superheated in superheater 8 using high pressure steam, and exits it in line 9 at a pressure of 14.8 bar absolute (14.8×10$^5$ Pa) and at a temperature of 235° C. Line 9 leads to a first dehydrogenation reactor 10 which contains a charge of a reduced copter oxide catalyst. A suitable catalyst is that sold under the designation E408Tu by Mallinckrodt Specialty Chemicals, Inc. In passage through first dehydrogenation reactor 10 the mixture of ethanol and hydrogen is partly converted by dehydrogenation according to equation (3) above to form ethyl acetate. This dehydrogenation reaction is endothermic.

The first intermediate dehydrogenation mixture exits reactor 10 in line 11 at a temperature in the range of from 205° C. to 220° C. and is reheated in heater 12 under the influence of high pressure steam. The reheated mixture flows on in line 13 to a second dehydrogenation reactor 14 which also contains a charge of the same dehydrogenation catalyst as that in reactor 10. Further dehydrogenation of ethanol to ethyl acetate occurs in passage through second dehydrogenation reactor 14.

A second intermediate dehydrogenation mixture containing ethyl acetate, unreacted ethanol and hydrogen exits reactor 14 in line and is reheated in reheater 16 which is heated by means of high pressure steam. The reheated stream flows on in line 17 to a third dehydrogenation reactor 18 which contains a charge of the same dehydrogenation catalyst as is present in reactors and 14.

The resulting third intermediate reaction mixture flows on in line 19 to heat exchanger which is also heated by means of high pressure steam. The reheated mixture passes on in line 21 to fourth dehydrogenation reactor 22 which contains a further charge of the same dehydrogenation catalyst that is loaded into the first, second and third dehydrogenation reactors 10, 14, and 18.

A crude product mixture exits fourth dehydrogenation reactor 22 in line 23, is cooled in passage through a heat exchanger 24, and emerges in line 25 at a temperature of 60° C. and at a pressure of 11.3 bar ($11.3 \times 10^5$ Pa) absolute.

The crude product mixture in line 25 comprises hydrogen, ethyl acetate, unconverted ethanol, water and minor amounts of impurities present either from contamination in the feed or recycle streams or from side reactions in reactors 10, 14, 18 and 22. Examples of these impurities include iso-propanol, acetaldehyde, diethyl ether, methanol, acetone, di-iso-propyl ether, n-butyraldehyde, butan-2-one, sec-butanol, iso-propyl acetate, pentan-2-one, n-butanol, sec-pentanol, sec-butyl acetate, ethyl butyrate, n-butyl acetate and di-n-butyl ether. Of particular significance in relation to this invention are those impurities whose boiling points are close to that of ethyl acetate or which form azeotropic mixtures with ethyl acetate. These include ethanol, as well as certain carbonyl-containing compounds such as acetone, acetaldehyde and butan-2-one.

The crude mixture in line 25 flows into a knockout pot 26 which is provided with a condenser (not shown) supplied with chilled coolant. The uncondensed gases, which are now at a temperature of −10° C., are recovered in line 27. A part of these gases is recycled in line 28 and compressed by means of gas recycle compressor 29 to a pressure of 15.5 bar ($1.55 \times 10^6$ Pa) absolute to form the gas stream in line 6 for supply to the first dehydrogenation reactor 10. Another part is taken in line 30 for a purpose which will be described hereunder. A purge stream is taken in line 31.

The condensate is removed from knockout pot 26 in line 32 and is pumped by a pump (not shown) to heat exchanger 33. The resulting re-heated liquid, now at a temperature of 60° C. to 80° C., is fed via line 34 and mixed with a hydrogen-containing gas which is at a temperature of 119° C. and has been compressed by a second gas compressor 35 to a pressure of 43.1 bar ($4.31 \times 10^6$ Pa) absolute so as to pass along line 36. The resulting mixture flows on in line 37 into a reactor 38 which contains a charge of a selective hydrogenation catalyst which is chosen so as selectively to hydrogenate reactive carbonyl-containing compounds, such as n-butyraldehyde, butan-2-one and the like, to the respective corresponding alcohols but not to effect any significant hydrogenation of ethyl acetate to ethanol. The inlet temperature to reactor 37 is adjusted as necessary to a temperature in the range of from 60° C. to 80° C. in dependance upon the degree of deactivation of the catalyst but is chosen to be as low as possible consistent with obtaining an acceptable reaction rate because the equilibrium is favorable at lower temperatures than at high temperatures. A preferred catalyst is 5% ruthenium on carbon available from Engelhard.

The resulting selectively hydrogenated reaction product is now essentially free from reactive carbonyl compounds, such as aldehydes and ketones, and exits reactor 38, in admixture with unreacted hydrogen, in line 39 at a, temperature of 70° C. to 90° C. This line leads to a lower part of a first distillation column 40 which is maintained at a pressure of 1.5 bar ($1 \times 10^5$ Pa) absolute. A bottoms product is withdrawn from distillation column 40 in line 41. Part of this is recycled to distillation column through line 42, column reboiler 43 and line 44. The remainder is passed by way of line 45 to a purification section (or water removal package) 46 in which it is treated in any convenient manner for the removal of water (and possibly other impurities) therefrom so as to yield a stream of moderately dry ethanol for recycle to the first dehydrogenation reactor 10 by way of line 2. The precise design of water removal package 46 will depend upon the composition of the ethanol feed stream in line 1. The bottoms product in line 41 typically comprises mainly ethanol with minor amounts of, for example, iso-propanol, water, $C_{4+}$ alkanols, and traces or ketones, other esters and ethers.

An overhead stream, which typically comprises a major proportion of diethyl ether and lesser amounts of other ethers, methanol, ethanol, n-butyraldehyde, and alkanes, as well as traces of acetaldehyde, ethyl acetate, and water, is recovered in line 47 and condensed by means of condenser 48. Uncondensed gases are purged in line 49, while the resulting condensate is recycled to the top of distillation column 40 as a reflux stream in line 50. A side draw stream is taken from distillation column 40 in line 51 and pumped by a pump (not shown) to a second distillation column 52 which is maintained at an overhead pressure of 12 bar ($1.2 \times 10^6$ Pa) absolute.

From the bottom of distillation column 52 a stream comprising substantially pure ethyl acetate is recovered in line 53, part of which is recycled to a lower part of distillation column 52 by way of line 54, column reboiler 55, and line 56. The remainder forms the product stream in line 57 from the plant; this can be taken to storage or further distilled in one or more further distillation columns, if desired, in order to remove minor amounts of iso-propyl acetate, di-propyl ether, and 1-ethoxybutane.

An overhead product consisting mainly of ethanol, ethyl acetate and water, besides smaller amounts of 1-ethoxybutane, methanol, diethyl ether and di-propyl ether and traces of alkanes, is taken in line 58 and condensed by means of condenser 59. The resulting condensate passes on in line 60, some being recycled to the first distillation column by way of line 61 while the remainder is recycled as a reflux stream to the second distillation column 52 in line 62. Reference numeral 63 indicates a line for recovery of water and other materials from water removal package 46.

The compositions in mol % of some of the more important streams in the plant of FIG. 1 are set out in Table 2 below.

TABLE 2

| | Stream | | | | | | | | | | | | | |
|---|---|---|---|---|---|---|---|---|---|---|---|---|---|---|
| | 1 | 2 | 9 | 25 | 27 | 32 | 37 | 39 | 45 | 49 | 51 | 57 | 61 | 63 |
| Hydrogen | 0.00 | 0.00 | 1.96 | 32.43 | 95.67 | 0.24 | 5.32 | 3.26 | 0.00 | 64.41 | 0.00 | 0.00 | 0.00 | 0.00 |
| Carbon monoxide | 0.00 | 0.00 | 0.01 | 0.17 | 0.49 | 0.00 | 0.03 | 0.03 | 0.00 | 0.64 | 0.00 | 0.00 | 0.00 | 0.00 |
| Water | 0.13 | 0.13 | 0.13 | 1.20 | 0.04 | 1.80 | 1.71 | 1.73 | 2.26 | 0.93 | 3.94 | 0.00 | 5.36 | 39.80 |
| Methanol | 0.01 | 0.00 | 0.01 | 0.01 | 0.00 | 0.01 | 0.01 | 0.01 | 0.00 | 0.20 | 0.06 | 0.00 | 0.09 | 0.00 |
| Ethanol | 99.84 | 99.84 | 97.82 | 49.25 | 1.39 | 73.50 | 69.67 | 72.70 | 96.52 | 16.76 | 50.42 | 0.02 | 68.73 | 37.90 |

TABLE 2-continued

| | Stream | | | | | | | | | | | | | |
|---|---|---|---|---|---|---|---|---|---|---|---|---|---|---|
| | 1 | 2 | 9 | 25 | 27 | 32 | 37 | 39 | 45 | 49 | 51 | 57 | 61 | 63 |
| Ethyl acetate | 0.00 | 0.00 | 0.01 | 15.03 | 0.91 | 22.32 | 21.18 | 20.86 | 0.00 | 7.17 | 45.40 | 99.98 | 25.57 | 0.00 |
| Acetaldehyde | 0.00 | 0.00 | 0.00 | 0.51 | 0.03 | 0.75 | 0.71 | 0.01 | 0.00 | 0.13 | 0.14 | 0.00 | 0.19 | 0.00 |
| Ethane | 0.00 | 0.00 | 0.00 | 0.09 | 0.20 | 0.03 | 0.04 | 0.04 | 0.00 | 0.82 | 0.00 | 0.00 | 0.00 | 0.00 |
| Methane | 0.00 | 0.00 | 0.03 | 0.41 | 1.17 | 0.03 | 0.09 | 0.09 | 0.00 | 1.78 | 0.00 | 0.00 | 0.00 | 0.00 |
| Di-ethyl ether | 0.01 | 0.00 | 0.01 | 0.27 | 0.09 | 0.37 | 0.35 | 0.36 | 0.00 | 7.09 | 0.04 | 0.00 | 0.06 | 0.00 |
| n-butyr-aldehyde | 0.00 | 0.00 | 0.00 | 0.01 | 0.00 | 0.01 | 0.01 | 0.00 | 0.00 | 0.00 | 0.00 | 0.00 | 0.00 | 0.00 |
| n-butanol | 0.00 | 0.01 | 0.00 | 0.12 | 0.00 | 0.18 | 0.17 | 0.19 | 0.25 | 0.01 | 0.00 | 0.00 | 0.00 | 4.53 |
| sec-butanol | 0.00 | 0.01 | 0.00 | 0.26 | 0.00 | 0.38 | 0.36 | 0.51 | 0.67 | 0.05 | 0.00 | 0.00 | 0.00 | 12.15 |
| Butan-2-one | 0.01 | 0.00 | 0.01 | 0.10 | 0.01 | 0.14 | 0.14 | 0.00 | 0.00 | 0.00 | 0.00 | 0.00 | 0.00 | 0.00 |
| n-butyl acetate | 0.00 | 0.00 | 0.00 | 0.05 | 0.00 | 0.08 | 0.07 | 0.07 | 0.10 | 0.01 | 0.00 | 0.00 | 0.00 | 1.81 |
| sec-butyl acetate | 0.00 | 0.00 | 0.00 | 0.02 | 0.00 | 0.03 | 0.03 | 0.03 | 0.04 | 0.00 | 0.00 | 0.00 | 0.00 | 0.73 |
| Ethyl butyrate | 0.00 | 0.00 | 0.00 | 0.04 | 0.00 | 0.07 | 0.06 | 0.06 | 0.09 | 0.00 | 0.00 | 0.00 | 0.00 | 1.63 |
| Di-butyl ether | 0.00 | 0.00 | 0.00 | 0.00 | 0.00 | 0.01 | 0.01 | 0.01 | 0.01 | 0.00 | 0.00 | 0.00 | 0.00 | 0.18 |
| n-hexanol | 0.00 | 0.00 | 0.00 | 0.00 | 0.00 | 0.00 | 0.00 | 0.00 | 0.01 | 0.00 | 0.00 | 0.00 | 0.00 | 0.18 |
| iso-butanol | 0.00 | 0.01 | 0.01 | 0.01 | 0.00 | 0.01 | 0.01 | 0.01 | 0.01 | 0.00 | 0.00 | 0.00 | 0.00 | 0.18 |
| Others | 0.00 | 0.00 | 0.00 | 0.02 | 0.00 | 0.04 | 0.03 | 0.03 | 0.04 | 0.00 | 0.00 | 0.00 | 0.00 | 0.91 |
| Total | 100.00 | 100.00 | 100.00 | 100.00 | 100.00 | 100.00 | 100.00 | 100.00 | 100.00 | 100.00 | 100.00 | 100.00 | 100.00 | 100.00 |

Figure 2:
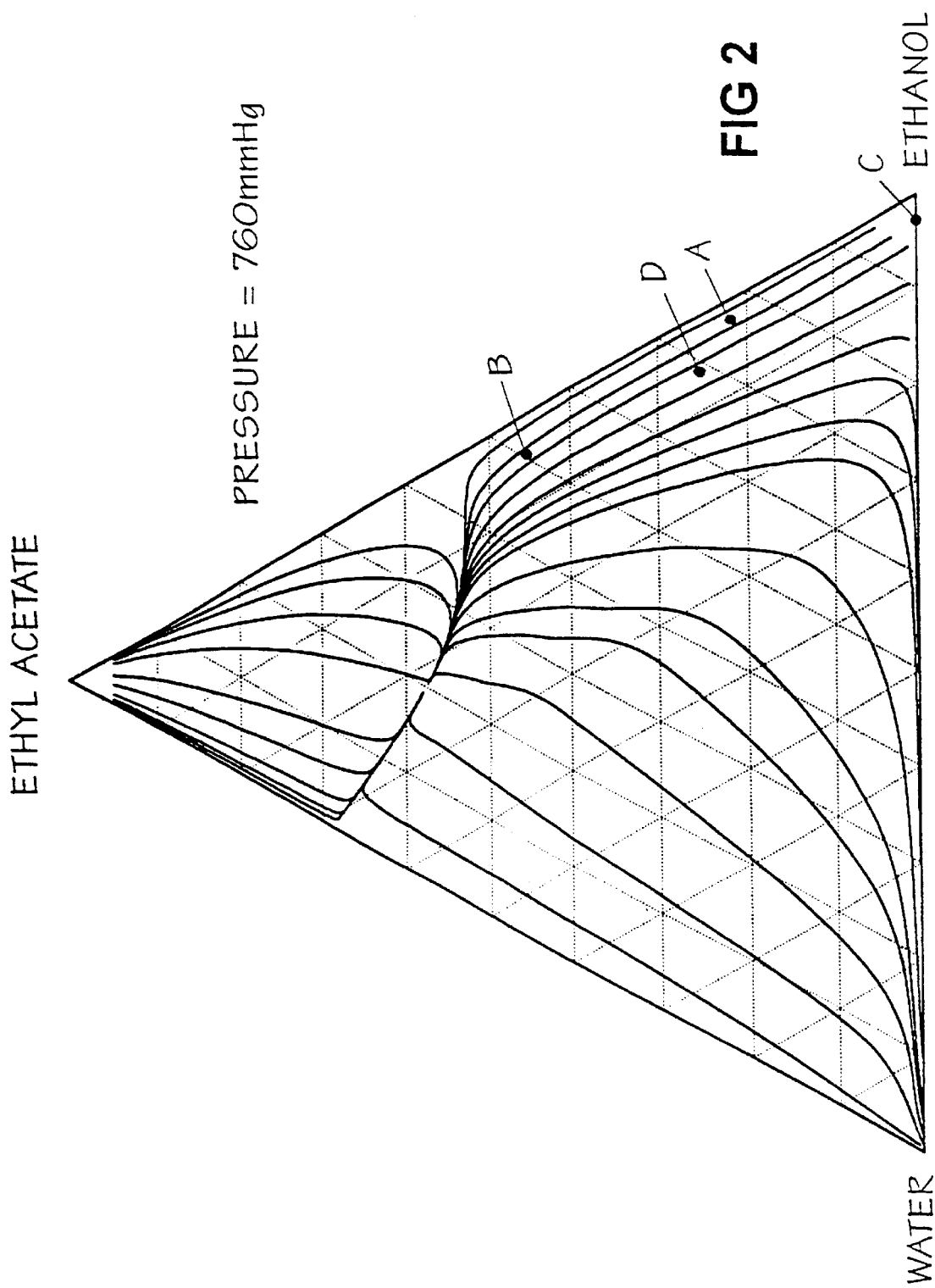

FIG. 2 is a triangular diagram illustrating the distillation characteristics of mixtures of ethanol, water and ethyl acetate at 760 mm Hg ($1.01 \times 10^6$ Pa) in which are plotted distillation lines for different mixtures of the three components. FIG. 3 is a similar diagram illustrating the distillation characteristics of the same ternary system at 9308 mm Hg ($12.41 \times 10^6$ Pa) It will be noted that there are significant differences between the distillation lines observed at different operating pressures. In FIG. 2 the composition of a typical feed as might be supplied in line 39 of the plant of FIG. 1 is indicated by point A. Point B indicates the composition of the side draw stream in line 51 for this feed. Point C indicates the composition of the resulting bottom stream in line 41 and point D indicates the composition of the stream in line 61. The effective feed composition to column 40 lies on the intersection of the straight line joining A and D with the straight line joining points B and C. In FIG. 3 the points B and D represents the same compositions as the corresponding points in the triangular diagram of FIG. 2. Point E represents the composition of the substantially pure ethyl acetate recovered in line 45.

The invention is further described in the following

EXAMPLES

Examples 1 to 5

These Examples investigated the dehydrogenation of ethanol to ethyl acetate in the presence of hydrogen. The apparatus used included a dehydrogenation reactor made of stainless steel tubing which contained a charge of reduced copper oxide catalyst and which was immersed in a hot oil bath for heating purposes.

At start-up a charge of 200 ml of a tabulated copper oxide catalyst available under the designation E408Tu from Mallinckrodt Specialty Chemicals was placed in the reactor which was then purged with nitrogen at 14.5 bar ($14.5 \times 10^5$ Pa) A dilute $H_2$ in $N_2$ gaseous mixture at 3 bar ($3 \times 10^5$ Pa) was passed over the catalyst at a rate of 600 standard liters per hour for 60 hours in order to effect catalyst reduction. The oil bath was raised to the temperature indicated in Table 3 below. The gas feed was then changed to pure hydrogen.

In operation hydrogen was introduced to the dehydrogenation reactor at rate of 2 standard liters per hour by way of a pressure regulator and flow controller through a line which was immersed in the bottom of the oil bath. An ethanol stream whose composition is set out in Table 3 was fed as a liquid at a rate of 200 ml/hr to a vaporiser and mixed with the hydrogen. The resulting vaporous mixture of ethanol and hydrogen was supplied to the dehydrogenation reactor.

The reaction products were cooled and the liquid condensate was analysed by gas chromatography. The results obtained are summarised in Table 3.

TABLE 3

| | | Example No | | | | |
|---|---|---|---|---|---|---|
| | Feed | 1 | 2 | 3 | 4 | 5 |
| Temperature (° C.) | — | 225 | 224 | 224 | 223 | 224 |
| Pressure (bar) ($10^5$ Pa) | — | 4.53 | 2.74 | 7.91 | 28.6 | 47.0 |
| Product Analysis (wt %) | | | | | | |
| Acetaldehyde | 0.007 | 2.578 | 5.317 | 1.388 | 0.114 | 0.027 |
| Methanol | 0.064 | 0.063 | 0.087 | 0.034 | 0.013 | 0.011 |
| Di-ethyl ether | 0.108 | 0.133 | 0.120 | 0.139 | 0.167 | 0.185 |
| Ethanol | 95.093 | 63.184 | 66.778 | 64.050 | 67.236 | 72.676 |
| Acetone | 0.007 | 2.264 | 2.883 | 1.679 | 0.630 | 0.326 |
| iso-propanol | 3.403 | 1.582 | 1.081 | 2.114 | 3.210 | 3.511 |
| Di-iso-propyl ether | 0.116 | 0.139 | 0.134 | 0.138 | 0.136 | 0.138 |
| n-butyr-aldehyde | 0 | 0.012 | 0.010 | 0.006 | 0.004 | 0.005 |
| Ethyl acetate | 0.030 | 25.605 | 18.935 | 27.087 | 26.377 | 21.107 |
| Butan-2-one | 0.005 | 1.230 | 1.655 | 0.661 | 0.074 | 0.015 |
| sec-butanol | 0.004 | 0.768 | 0.543 | 0.761 | 0.360 | 0.174 |
| iso-propyl acetate | 0 | 0.184 | 0.144 | 0.040 | 0.316 | 0.318 |
| Pentan-2-one | 0 | 0.316 | 0.309 | 0.233 | 0.055 | 0.010 |
| n-butanol | 0.097 | 0.329 | 0.410 | 0.274 | 0.203 | 0.431 |
| sec-pentanol | 0 | 0.138 | 0.075 | 0.180 | 0.148 | 0.087 |
| sec-butyl acetate | 0 | 0.058 | 0.037 | 0.057 | 0.052 | 0.044 |
| Ethyl butyrate | 0 | 0.132 | 0.115 | 0.093 | 0.030 | 0.075 |
| n-butyl acetate | 0 | 0.123 | 0.096 | 0.086 | 0.022 | 0.076 |
| Water | 0.540 | 0.789 | 0.920 | 0.660 | 0.450 | 0.460 |
| Others | 0.526 | 0.373 | 0.351 | 0.320 | 0.403 | 0.324 |
| Total | 100.00 | 100.00 | 100.00 | 100.00 | 100.00 | 100.00 |

Examples 6 to 9

In these Examples the selective hydrogenation of reactive carbonyl compounds in the presence of ethyl acetate was investigated using a hydrogenation reactor constructed out of stainless steel which was immersed in a hot oil bath for heating purposes.

In operation hydrogen was introduced by way of a pressure regulator and flow controller to the reactor which contained a charge of an Englehard 5% ruthenium on carbon granular catalyst.

At start up a charge of 100 ml of the granular catalyst was placed in the reactor which was then supplied with hydrogen at a pressure of 7.9 bar ($7.9 \times 10^5$ Pa), and warmed to 180–200° C. from room temperature at a rate of 20° C. per hour. The reactor was held at 180–200° C. for one hour and then cooled. At the end of this procedure the catalyst was fully reduced.

Dehydrogenation reaction product mixture whose composition is set out under "Feed" in Table 4 was introduced to a heater at a rate of 130 ml/hr and admixed with 7.8 standard liters per hour of hydrogen prior to admission to the selective hydrogenation reactor. The reaction product was cooled and the liquid condensate was analysed by gas chromatography. The results are summarised in Table 4.

TABLE 4

| | Feed | Example No 6 | 7 | 8 | 9 |
|---|---|---|---|---|---|
| Reactor Temperature (° C.) | — | 91 | 80 | 72 | 110 |
| Pressure (bar) ($10^5$ Pa) | — | 14.2 | 14.2 | 14.4 | 14.1 |
| Product Analysis (Wt %) | | | | | |
| Acetaldehyde | 0.904 | 0.034 | 0.040 | 0.038 | 0.039 |
| Diethyl ether | 0.579 | 0.428 | 0.418 | 0.417 | 0.419 |
| Ethanol | 68.223 | 70.040 | 70.121 | 70.163 | 70.301 |
| Acetone | 2.282 | trace | trace | trace | trace |
| iso-propanol | 1.004 | 3.232 | 3.233 | 3.213 | 3.231 |
| Di-iso-propyl ether | 0.003 | 0.098 | 0.097 | 0.097 | 0.097 |
| n-butyraldehyde | 0.010 | trace | trace | trace | trace |
| Ethyl acetate | 23.263 | 22.572 | 22.464 | 22.437 | 22.396 |
| Butan-2-one | 0.170 | 0.002 | 0.004 | 0.007 | 0.003 |
| sec-butanol | 0.371 | 0.567 | 0.566 | 0.560 | 0.567 |
| iso-propyl acetate | 0.186 | 0.185 | 0.184 | 0.184 | 0.184 |
| n-butanol | 0.507 | 0.730 | 0.770 | 0.776 | 0.570 |
| Water | 1.410 | 1.170 | 1.170 | 1.200 | 1.270 |
| Others | 1.088 | 0.942 | 0.933 | 0.908 | 0.923 |
| Total | 100.00 | 100.00 | 100.00 | 100.00 | 100.00 |

Notes:
The increased amount of n-butanol noted in Examples 6 to 9 compared with the amount in the feed can be ascribed not only to n-butanol formed by hydrogenation of n-butyraldehyde present in the feed (the amount of which is, in any case, difficult to measure) but also from hydrogenation of other products which contain $C_4$ groups and which are included in the figure given for "others" in the feed.

Examples 10 to 12

The general procedure of Examples 6 to 9 was repeated using a different feed and different reaction conditions. The results are set out in Table 5 below.

TABLE 5

| | Feed | Example No 10 | 11 | 12 |
|---|---|---|---|---|
| Reactor Temperature (° C.) | — | 79 | 98 | 119 |
| Pressure (bar) ($10^5$ Pa) | — | 42.6 | 42.1 | 42.5 |
| Product Analysis (Wt %) | | | | |
| Acetaldehyde | 0.952 | 0.006 | 0.006 | 0.006 |
| Diethyl ether | 0.030 | 0.030 | 0.029 | 0.033 |
| Ethanol | 64.703 | 65.930 | 66.034 | 65.627 |
| Acetone | trace | 0 | 0 | 0 |
| iso-propanol | 0.022 | 0.032 | 0.035 | 0.038 |
| n-butyraldehyde | trace | 0 | 0 | 0 |
| Ethyl acetate | 31.692 | 31.410 | 31.155 | 31.409 |
| Butan-2-one | 0.301 | trace | trace | 0.001 |
| sec-butanol | 0.487 | 0.803 | 0.806 | 0.810 |
| n-butanol | 0.560 | 0.588 | 0.596 | 0.573 |
| Water | 0.620 | 0.600 | 0.700 | 0.890 |
| Others | 0.633 | 0.601 | 0.639 | 0.613 |
| Total | 100.00 | 100.00 | 100.00 | 100.00 |

Example 13

A mixture containing ethanol, water, ethyl acetate and other components was distilled in a continuous feed laboratory distillation apparatus having the general layout of columns 40 and 52 of FIG. 1, except that line 51 received condensate from line 50, rather than a side draw stream from an outlet positioned somewhat lower in column 40. A bleed of $O_2$-free nitrogen was supplied to column 40 so as to ensure that oxygen was excluded from column 40 in order to prevent oxidation of any oxygen-sensitive components in the feed in line 39 such as aldehydes. Hence column 40 was operated at a few milliards over atmospheric pressure. The feed to column was vaporiser in a stream of $O_2$-free nitrogen prior to introduction into column 40. The reflux temperature in column 40 was 64° C., the overhead temperature was 72° C. and the temperature at the bottom of the column was 73° C. The reflux ratio was 5:1. The operating pressure in column 52 was 12.4 bar ($1.24 \times 10^6$ Pa gauge). The overhead temperature was 160° C., the reflux temperature was 153° C. and the boiler temperature was 204° C. The reflux ratio was 2.8:1. The distillation column had 3 thermocouples positioned near the top, at the mid point and near the bottom, the readings of which were 163° C., 180° C. and 180° C. respectively. The results obtained are listed in Table 6 in which amounts are in % by weight.

TABLE 6

| | Line No. 39 | 51 | 41 | 61 | 53 |
|---|---|---|---|---|---|
| Acetaldehyde | 0.009 | 0.007 | 0.013 | 0.446 | |
| Methanol | 0.090 | 0.141 | | 0.199 | |
| Diethyl ether | 0.073 | 0.113 | | 0.226 | |
| Ethanol | 57.626 | 31.077 | 96.579 | 71.382 | 0.064 |
| iso-propanol | 0.027 | | 0.087 | | |
| Ethyl acetate | 40.514 | 68.021 | 0.018 | 24.811 | 99.890 |
| Butan-2-ol | 0.548 | | 1.499 | | |
| n-butanol | 0.192 | 0.021 | 0.519 | | 0.010 |
| Ethyl butyrate | 0.117 | | 0.307 | | |
| Butyl acetate | 0.136 | | 0.358 | | |
| Water | 0.550 | 0.590 | 0.330 | 2.920 | 0.010 |
| "Light" unknowns | 0.020 | 0.029 | | 0.003 | |
| "Heavy" unknowns | 0.098 | 0.001 | 0.290 | 0.013 | 0.026 |
| Total | 100.00 | 100.00 | 100.00 | 100.00 | 100.00 |

What is claimed is:

1. A process for the purification of an impure feedstock comprising an alkyl alkanoate which contains not more than 12 carbon atoms, the process comprising:

(a) providing an impure feedstock containing an alkyl alkanoate which contains not more than 12 carbon atoms and at least one of an alkanol and water, said feedstock further containing at least one impurity selected from the group consisting of aldehydes and ketones which contain the same number of carbon atoms as said alkyl alkanoate;

(b) contacting said impure feedstock with a selective hydrogenation catalyst in the presence of hydrogen in a selective hydrogenation zone maintained under selective hydrogenation conditions effective for selective hydrogenation of said impurities thereby to hydrogenate said impurities to the corresponding alcohols;

(c) recovering from the selective hydrogenation zone a selectively hydrogenated reaction product mixture comprising said alkyl alkanoate, hydrogen, and said corresponding alcohols;

(d) distilling material of the selectively hydrogenated reaction product mixture in at least one distillation zone so as to produce purified alkyl alkanoate therefrom; and (e) recovering said purified alkyl alkanoate.

2. A process according to claim 1, in which the impure feedstock comprises a reaction product obtained by converting an alkanol to said alkyl alkanoate by a procedure selected from the group consisting of:

(i) dehydrogenation, (ii) oxidation, (iii) reaction with an aldehyde, and (iv) oxidation to the corresponding aldehyde followed by the Tischenko reaction.

3. A process according to claim 1, in which said alkyl alkanoate is a $C_{2+}$ alkyl $C_{2+}$ alkanoate.

4. A process according to claim 1, in which said alkyl alkanoate is selected from the group consisting of ethyl acetate, n-propyl propionate, and n-butyl butyrate.

5. A process according to claim 1, in which said alkyl alkanoate is ethyl acetate.

6. A process according to claim 1, in which the selective hydrogenation conditions of step (b) include use of a feedstock:hydrogen molar ratio of from about 1000:1 to about 1:1, a combined partial pressure of feedstock and hydrogen of from about 5 bar ($5 \times 10^5$ Pa) to about 80 bar ($8 \times 10^6$ Pa), and a temperature in the range of from about 40° C. to about 120° C.

7. A process according to claim 6, in which the combined partial pressure of feedstock and hydrogen in step (b) is from about bar 25 ($2.5 \times 10^6$ Pa) to about 50 bar ($5 \times 10^6$ Pa).

8. A process according to claim 1, in which the selective hydrogenation catalyst comprises a metal selected from the group consisting of nickel, palladium, platinum, ruthenium, rhodium and rhenium.

9. A process according to claim 8, in which the catalyst comprises ruthenium on carbon.

10. A process according to claim 1, in which the rate of supply of impure feedstock to the selective hydrogenation zone corresponds to a liquid hourly space velocity (LHSV) of from about 0.1 $hr^{-1}$ to about 2.0 $hr^{-1}$.

11. A process according to claim 1, in which the impure feedstock is an impure ethyl acetate feedstock which contains, in addition to ethyl acetate and impurities, also water and ethanol and in which step (d) comprises supplying material of the selectively hydrogenated reaction product mixture to a first distillation zone maintained under distillation conditions effective for distillation therefrom of a first distillate comprising ethyl acetate, ethanol and water, recovering a first distillate comprising ethyl acetate, ethanol, and water from the first distillation zone and a bottom product comprising ethanol and water, supplying material of the first distillate to a second distillation zone maintained under distillation conditions effective for distillation therefrom of a second distillate comprising ethanol, water, and ethyl acetate and so as to yield a purified ethyl acetate bottom product, and recovering a purified ethyl acetate bottom product from the second distillation zone.

12. A process according to claim 11, in which the first distillation zone is operated at a pressure of less than about 4 bar ($4 \times 10^5$ Pa).

13. A process according to claim 11, in which the first distillation zone is operated at a pressure of from about 1 bar ($10^5$ Pa) to about 2 bar ($2 \times 10^5$ Pa).

14. A process according to claim 11, in which the second distillation zone is operated at a pressure of from about 4 bar ($4 \times 10^5$ Pa) to about 25 bar ($2.5 \times 10^6$ Pa).

15. A process according to claim 11, in which the second distillation zone is operated at a pressure of from about 9 bar ($9 \times 10^5$ Pa) to about 15 bar ($15 \times 10^5$ Pa).

16. A process according to claim 11, in which an ethanol rich stream is recovered from the bottom of the first distillation zone, while an overhead stream that contains light components having lower boiling points than ethyl acetate and its azeotropes with water and ethanol present in the selectively hydrogenated reaction product mixture is recovered from the first distillation zone, and in which the first distillate comprises a liquid draw stream which is recovered an from an upper region of the first distillation zone and which comprises ethyl acetate, ethanol, and water.

17. A process according to claim 16, in which the ethanol rich stream recovered from the bottom of the first distillation zone is subjected to treatment for the removal of water therefrom.

18. A process according to claim 16, in which the first distillate contains from about 40 mol % to about 55 mol % ethyl acetate, from about 1 mol to about 6 mol % water, not more than about 1 mol % other components, and the balance ethanol.

19. A process according to claim 16, in which the first distillate is passed to the second distillation zone which is operated at a pressure of from about 9 bar ($9 \times 10^5$ Pa) absolute to about 15 bar ($1.5 \times 10^6$ Pa) absolute.

20. A process according to claim 16, in which the second distillate is recovered as an overhead stream from the second distillation zone, while a bottom product comprising purified ethyl acetate is recovered from the second distillation zone, the second distillate being returned to the first distillation zone at a point above the feed point of the material of the selectively hydrogenated reaction product mixture.

21. A process according to claim 20, in which the bottom product from the second distillation zone contains from about 99.8 mol % to about 99.95 mol % ethyl acetate.

22. A process according to claim 1, in which step (d) comprises extractive distillation with an extractive agent comprising polyethylene glycol and at least one material selected from the group consisting of dipropylene glycol, diethylene glycol, and triethylene glycol.

23. A process according to claim 1, in which step (d) comprises extractive distillation in the presence of an extractive agent containing dimethyl sulfoxide.

24. A process for the production of an alkyl alkanoate containing not more than 12 carbon atoms by dehydrogenation of an alkanol, the process comprising:
   (i) contacting a vaporous mixture containing an alkanol and hydrogen with a dehydrogenation catalyst in a dehydrogenation zone maintained under dehydrogenation conditions effective for dehydrogenation of an alkanol to yield an alkyl alkanoate containing not more than 12 carbon atoms;
   (ii) recovering from the dehydrogenation zone an intermediate reaction mixture comprising hydrogen and liquefiable products comprising said alkyl alkanoate, said alkanol, hydrogen and impurities selected from the group consisting of aldehydes and ketones which contain the same number of carbon atoms as said alkyl alkanoate;
   (iii) contacting at least a portion of the liquefiable products of the intermediate reaction product mixture with a selective hydrogenation catalyst in the presence of hydrogen in a selective hydrogenation zone maintained under selective hydrogenation conditions effective for selective hydrogenation of said impurities thereby to hydrogenate said impurities to the corresponding alcohols;
   (iv) recovering from the selective hydrogenation zone a selectively hydrogenated reaction product mixture comprising said alkyl alkanoate, hydrogen, and said corresponding alcohols;
   (v) distilling material of the selectively hydrogenated reaction product mixture in at least one distillation zone so as to produce purified alkyl alkanoate therefrom; and
   (vi) recovering said purified alkyl alkanoate.

25. A process according to claim 24, wherein the dehydrogenation conditions include use of an alkanol:hydrogen molar ratio of from about 1:10 to about 1000:1, a combined partial pressure of alkanol and hydrogen of from about 3 bar ($3 \times 10^5$ Pa) up to about 50 bar ($5 \times 10^6$ Pa), and a temperature in the range of from about 100° C. to about 260° C.

26. A process according to claim 25, wherein the dehydrogenation conditions include use of a combined partial pressure o alkanol and hydrogen of at least about 6 bar ($6 \times 10^5$ Pa) up to about 30 bar ($3 \times 10^6$ Pa).

27. A process according to claim 24, in which the dehydrogenation conditions include use of a temperature of between about 200° C. and about 250° C.

28. A process according to claim 24, in which the dehydrogenation catalyst is a copper containing catalyst which comprises, before reduction, copper oxide on alumina.

29. A process according to claim 24, in which the rate of supply of the feedstock to the dehydrogenation zone corresponds to an alkanol liquid hourly space velocity (LHSV) of from about 0.5 hr$^{-1}$ to about 1.0 hr$^{-1}$.

30. A process according to claim 24, in which the impure feedstock contains water and ethanol and in which in step (d) there is recovered an ethanol stream for recycle to the dehydrogenation zone.

* * * * *